US009788751B2

(12) United States Patent
Li et al.

(10) Patent No.: US 9,788,751 B2
(45) Date of Patent: Oct. 17, 2017

(54) METHODS AND SYSTEMS FOR GENERATING INTEGRATED SUBSTRATE MAPS FOR CARDIAC ARRHYTHMIAS

(71) Applicant: St. Jude Medical, Cardiology Division, Inc., St. Paul, MN (US)

(72) Inventors: Wenwen Li, San Jose, CA (US); Erhan Erdemir, Maplewood, MN (US); Valtino Afonso, Oakdale, MN (US); Carlo Pappone, Cernusco Lombardone (IT); Dennis Morgan, Crystal, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/884,545

(22) Filed: Oct. 15, 2015

(65) Prior Publication Data
US 2016/0106336 A1 Apr. 21, 2016

Related U.S. Application Data

(60) Provisional application No. 62/063,989, filed on Oct. 15, 2014.

(51) Int. Cl.
*A61B 5/05* (2006.01)
*A61B 5/053* (2006.01)
(Continued)

(52) U.S. Cl.
CPC .......... *A61B 5/0536* (2013.01); *A61B 5/0422* (2013.01); *A61B 5/0452* (2013.01);
(Continued)

(58) Field of Classification Search
CPC .... A61B 5/04; A61B 5/72; A61B 5/74; A61B 6/03; A61B 18/14; G06T 7/00; G06F 19/32
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| EP | 2638853 | 9/2013 |
| WO | 2007/024983 | 3/2007 |

(Continued)

OTHER PUBLICATIONS

Greenhut, SE et al., "Comparison of new template matching algorithm, correlation, and area of difference methods for detection of ventricular tachycardia", Computers in cardiology, pp. 371-374, Oct. 1992.

(Continued)

*Primary Examiner* — Ankit D Tejani
(74) *Attorney, Agent, or Firm* — Wiley Rein LLP

(57) ABSTRACT

An electrophysiology map, for example a map of arrhythmic substrate, can be generated by acquiring both geometry information and electrophysiology information pertaining to an anatomical region, and associating the acquired geometry and electrophysiology information as a plurality of electrophysiology data points. A user can select two (or more) electrophysiological characteristics for display, and can further elect to apply various filters to the selected electrophysiological characteristics. The user can also define various relationships (e.g., Boolean ANDs, ORs, and the like) between the selected and/or filtered characteristics. The user-selected filtering criteria can be applied to the electrophysiology data points to output various subsets thereof. These subsets can then be graphically rendered using various combinations of colorscale, monochrome scale, and iconography, for example as a three-dimensional cardiac electrophysiology model.

12 Claims, 13 Drawing Sheets

(51) Int. Cl.
*A61B 5/042* (2006.01)
*A61B 5/0452* (2006.01)
*A61B 5/0408* (2006.01)
*A61B 5/00* (2006.01)

(52) U.S. Cl.
CPC ........ *A61B 5/04087* (2013.01); *A61B 5/0538* (2013.01); *A61B 5/7225* (2013.01); *A61B 5/7485* (2013.01); *A61B 5/725* (2013.01); *A61B 5/743* (2013.01); *A61B 5/746* (2013.01); *A61B 2505/05* (2013.01)

(56) References Cited

U.S. PATENT DOCUMENTS

| | | |
|---|---|---|
| 6,301,496 B1 | 10/2001 | Reisfeld |
| 6,368,285 B1 | 4/2002 | Osadchy et al. |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,515,954 B2 | 4/2009 | Harlev et al. |
| 7,885,707 B2 | 2/2011 | Hauck |
| 7,937,136 B2 | 5/2011 | Harlev et al. |
| 7,957,792 B2 | 6/2011 | Harlev et al. |
| 8,103,338 B2 | 1/2012 | Harlev et al. |
| 8,428,700 B2 | 4/2013 | Harlev et al. |
| 9,220,435 B2 | 12/2015 | Deno |
| 9,474,491 B2 | 10/2016 | Li et al. |
| 2005/0192972 A1 | 9/2005 | Daignault |
| 2007/0197929 A1 | 8/2007 | Porath et al. |
| 2008/0085042 A1 | 4/2008 | Trofimov et al. |
| 2008/0221425 A1 | 9/2008 | Olson et al. |
| 2009/0275826 A1 | 11/2009 | Shachar et al. |
| 2010/0021031 A1* | 1/2010 | Brockway ............ G06K 9/3233 382/128 |
| 2010/0130882 A1 | 5/2010 | Nakada et al. |
| 2011/0118590 A1 | 5/2011 | Zhang |
| 2011/0144510 A1 | 6/2011 | Ryu et al. |
| 2011/0184488 A1 | 7/2011 | De Ridder |
| 2011/0206256 A1 | 8/2011 | Ramanathan et al. |
| 2012/0108994 A1 | 5/2012 | Patel et al. |
| 2012/0130267 A1 | 5/2012 | Harlev et al. |
| 2012/0184858 A1 | 7/2012 | Harlev et al. |
| 2012/0184863 A1 | 7/2012 | Harlev et al. |
| 2012/0265054 A1 | 10/2012 | Olson |
| 2013/0241929 A1 | 9/2013 | Massarwa et al. |
| 2014/0200467 A1 | 7/2014 | Strom et al. |
| 2014/0200874 A1 | 7/2014 | Zeng et al. |
| 2015/0157267 A1 | 6/2015 | Shushan et al. |
| 2015/0228254 A1 | 8/2015 | Olson |
| 2016/0242667 A1 | 8/2016 | Fay et al. |

FOREIGN PATENT DOCUMENTS

| | | |
|---|---|---|
| WO | 2010/054320 | 5/2010 |
| WO | 2012/092016 | 7/2012 |

OTHER PUBLICATIONS

Kindlmann, G., Superquadric Tensor Glyphs, Joint Joint EUROGRAPHICS—IEEE TCVG Symposium on Visualization, 2004.

Krasteva, Vessels et al., "QRS template matching for recognition of ventricular ectopic beats", Annals of biomedical engineering, vol. 35, No. 12, pp. 2065-2076, Dec. 2007.

* cited by examiner

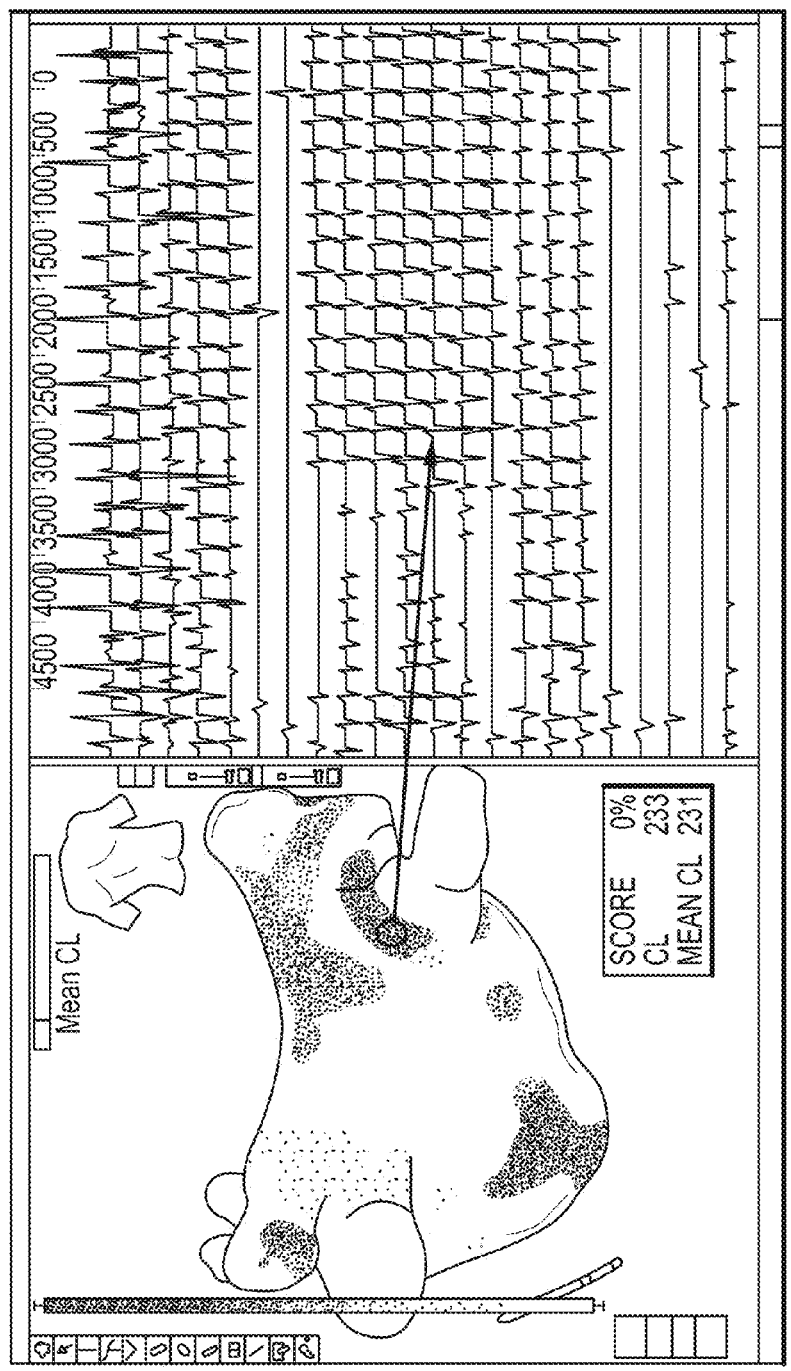

METHODS AND SYSTEMS FOR GENERATING INTEGRATED SUBSTRATE MAPS FOR CARDIAC ARRHYTHMIAS

CROSS-REFERENCE TO RELATED APPLICATIONS

This application claims the benefit of U.S. provisional application No. 62/063,989, filed 15 Oct. 2014, which is hereby incorporated by reference as though fully set forth herein.

BACKGROUND

The instant disclosure relates to anatomical mapping. In particular, the instant disclosure relates to systems, apparatuses, and methods for creating electrophysiology maps, such as may be useful in cardiac diagnostic and therapeutic procedures.

Two mainstay hypotheses of arrhythmia maintenance mechanisms are single source focus and circus movement reentry. However, the mechanisms and substrates that maintain atrial fibrillation can vary from patient-to-patient. Thus, there is a need for apparatuses, systems, and methods that facilitate the identification, classification, and characterization of multiple arrhythmic mechanisms and substrates.

BRIEF SUMMARY

Disclosed herein is a method of generating an electrophysiology map, including: acquiring geometry information pertaining to an anatomical region, the geometry information including position information for a plurality of points in the anatomical region; acquiring electrophysiology information pertaining to the anatomical region, the electrophysiology information including a plurality of electrophysiological characteristics of the anatomical region; associating the geometry information with the electrophysiology information as a plurality of electrophysiology ("EP") data points; accepting user input to select a first electrophysiological characteristic of the plurality of electrophysiological characteristics and a first filtering criterion for the first electrophysiological characteristic; accepting user input to select a second electrophysiological characteristic of the plurality of electrophysiological characteristics and a second filtering criterion for the second electrophysiological characteristic; applying the first filtering criterion and the second filtering criterion to the plurality of EP data points; and outputting a subset of the plurality of EP data points satisfying both the first filtering criterion and the second filtering criterion. For example, the first electrophysiological characteristic can be cycle length mean and the second electrophysiological characteristic can be cycle length standard deviation. Similarly, the first filtering criterion can be a band pass filter with a pass band from 110 ms to 290 ms (e.g., between about 150 ms and about 250 ms), and the second filtering criterion can be a band pass filter with a pass band from 1 ms to 30 ms.

In other embodiments, the first and second electrophysiological characteristics and their respective filtering criteria can be selected from the following pairings of electrophysiological characteristics and filtering criteria: fractionation index and a high pass filter; peak-to-peak voltage and a low pass filter; electrogram sharpness and a high pass filter; conduction velocity consistency index and a high pass filter; and conduction velocity and a low pass filter.

It is also contemplated that a three-dimensional graphical representation of the subset of the plurality of EP data points can be output. For example, a user can provide input to prioritize the first electrophysiological characteristic and the second electrophysiological characteristic, such that the graphical representation of the subset of the plurality of EP data points is rendered according to the prioritization of the first electrophysiological characteristic and the second electrophysiological characteristic (e.g., with higher priority electrophysiological characteristics drawn preferentially to lower priority electrophysiological characteristics at any given point on the graphical representation).

Also disclosed herein is a method of generating an electrophysiology map, including: acquiring geometry information pertaining to an anatomical region, the geometry information including position information for a plurality of points in the anatomical region; acquiring electrophysiology information pertaining to the anatomical region, the electrophysiology information including a plurality of electrophysiological characteristics of the anatomical region; associating the geometry information with the electrophysiology information as a plurality of electrophysiology ("EP") data points; accepting user input to select a first electrophysiological characteristic of the plurality of electrophysiological characteristics, a first filtering criterion for the first electrophysiological characteristic, and a first priority for the first electrophysiological characteristic; applying the first filtering criterion to the plurality of EP data points to output a first subset of the plurality of EP data points satisfying the first filtering criterion; accepting user input to select a second electrophysiological characteristic of the plurality of electrophysiological characteristics, a second filtering criterion for the second electrophysiological characteristic, and a second priority for the second electrophysiological characteristic; applying the second filtering criterion to the plurality of EP data points to output a second subset of the plurality of EP data points satisfying the second filtering criterion; outputting a three-dimensional graphical representation of the first and second subsets of the plurality of EP data points according to the first priority and the second priority. For example, outputting a three-dimensional graphical representation of the first and second subsets of the plurality of EP data points according to the first priority and the second priority can include: rendering the graphical representation of the first subset of the plurality of EP data points preferentially to the graphical representation of the second subset of the plurality of data points if the first priority is higher than the second priority; and rendering the graphical representation of the second subset of the plurality of EP data points preferentially to the graphical representation of the first subset of the plurality of data points if the second priority is higher than the first priority. The graphical representations of the first and second subsets of the plurality of EP data points can be rendered using various combinations of colorscale, monochrome scale, and iconography.

It should also be understood that the teachings herein are not limited to two subsets of the plurality of EP data points, and can be extended to any number of electrophysiological characteristics and/or filters. Thus, for example, according to certain aspects of the disclosure, the method can further include: accepting user input to select a third electrophysiological characteristic of the plurality of electrophysiological characteristics, a third filtering criterion for the third electrophysiological characteristic, and a third priority for the third electrophysiological characteristic; applying the third filtering criterion to the plurality of EP data points to output a third subset of the plurality of EP data points satisfying the third filtering criterion; and outputting a three-dimensional graphical representation of the third subset of the plurality of EP data points according to the third priority. As with the first and second subsets of the plurality of EP data points, the third subset of the plurality of EP data points can likewise be output using various combinations of colorscale, monochrome scale, and iconography (e.g., one of the graphical representations of the first, second, and third subsets of the plurality of EP data points can be output in colorscale while the other two of the graphical representations of the first, second, and third subsets are output in monochrome scale).

According to yet another aspect disclosed herein, a system for generating an electrophysiology map includes: an electrophysiology data point processor configured to accept as input geometry information and electrophysiology information pertaining to an anatomical region and to associate the geometry information with the electrophysiology information as a plurality of electrophysiology data points; a filtering processor configured to accept as input a user's selection of n electrophysiological characteristics, wherein each of the n selected electrophysiological characteristics has an associated filtering criterion and an associated priority, and to apply the filtering criteria to their respective ones of the n selected electrophysiological characteristics; and a mapping processor configured to output a three-dimensional representation of the filtered n selected electrophysiological characteristics according to their respective priorities.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 5a through 5c illustrate the application of the EP data point filtering and electrophysiology map combination teachings herein with reference to cycle length mean and cycle length standard deviation.

DETAILED DESCRIPTION

The present disclosure relates to the collection and storage of data used to create anatomical maps and to the display of anatomical maps from the data so collected and stored, and provides methods, apparatuses, and systems for the storage and display of anatomical maps. As used herein, the term "anatomical map" refers to a graphical representation of an anatomical region that includes both a geometric model of the anatomical region and biological information of the anatomical region. For example, the biological information can be superimposed upon the geometric model. As used herein, the term "superimposed" means that the biological information is displayed over the geometric model and can, in some embodiments, be incorporated into the geometric model. In other embodiments, the biological information is not part of the geometric model itself, but rather "hovers" as an overlay upon the geometric model.

Electrophysiology maps, such as those that can be created using system 8 described below, are one type of anatomical map. For purposes of illustration, several exemplary embodiments will be described in detail herein in the context of a cardiac electrophysiology procedure, including the creation of cardiac electrophysiology maps. It is contemplated, however, that the methods, apparatuses, and systems disclosed herein can be utilized in other contexts.

Electrophysiology maps are generally created from a plurality of electrophysiology ("EP") data points, each of which includes both electrophysiology data (e.g., endocardial and/or epicardial electrograms ("EGMs")) and location data (e.g., information regarding the location of the apparatus (e.g., catheter and/or catheter-mounted electrodes) collecting the electrophysiology data, allowing the electrophysiology information to be associated with a particular location in space (that is, allowing the electrophysiology information to be interpreted as indicative of electrical activity at a point on the patient's heart). Insofar as the ordinarily skilled artisan will be familiar with various modalities for the acquisition and processing of EP data points (including, for example, both contact and non-contact electrophysiological mapping), as well as with various techniques that can be used to generate a graphical representation from the plurality of EP data points, these aspects will only be described herein to the extent necessary to understand the present disclosure.

Figure 1:
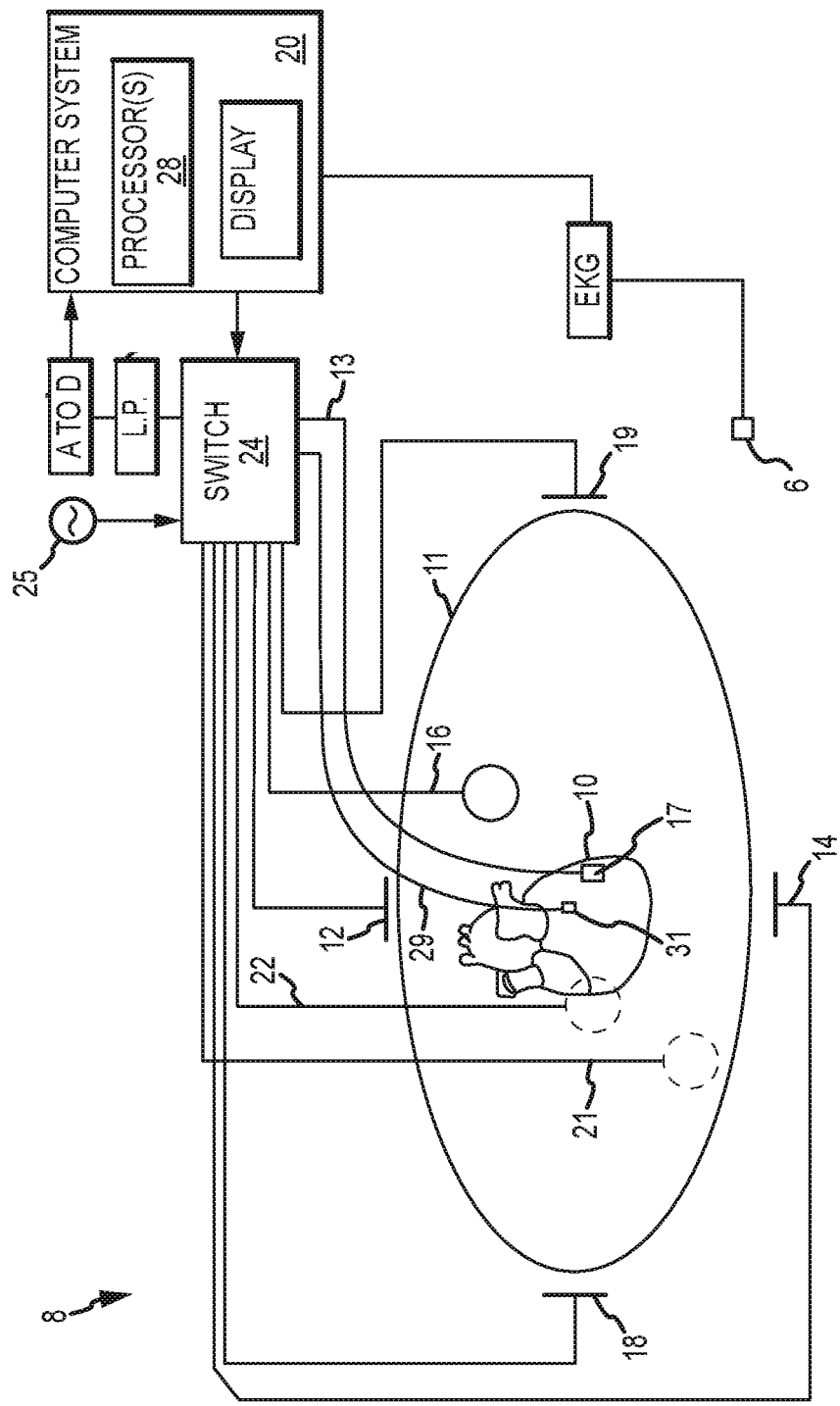
FIG. 1 is a schematic of an electrophysiology system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data, including various morphological characteristics, at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
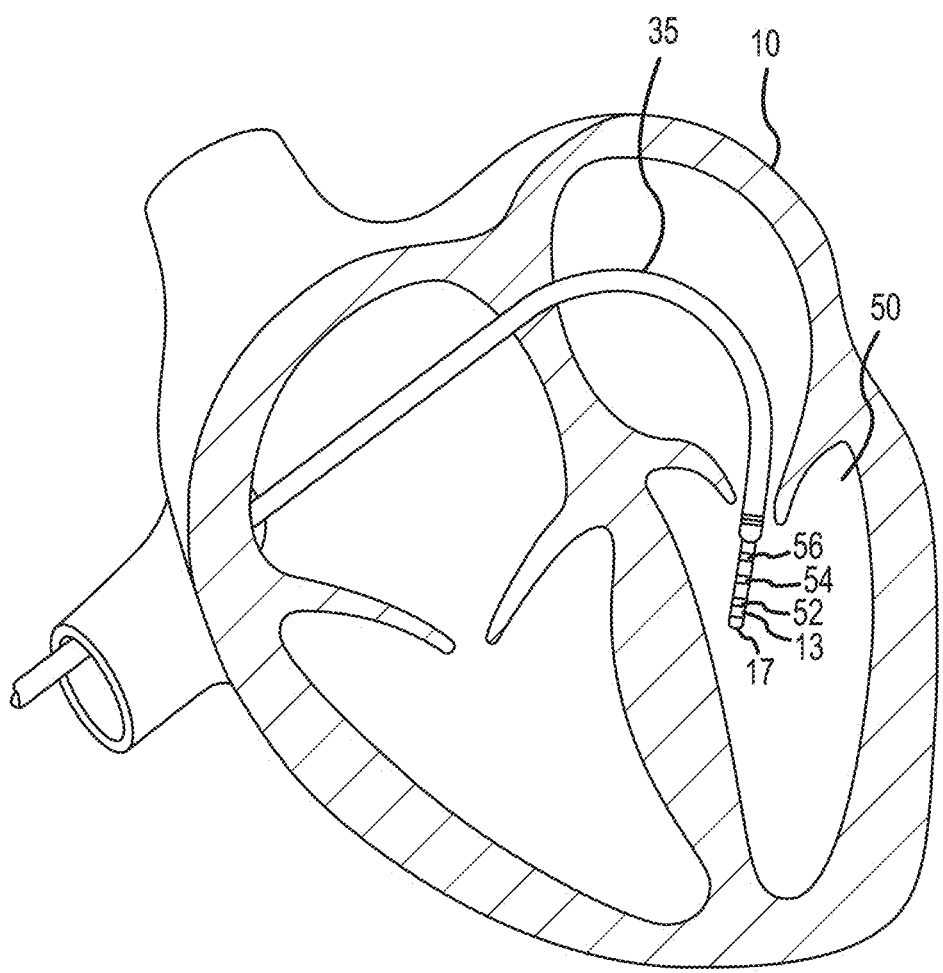
FIG. 2 depicts an exemplary multi-electrode catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8. Similarly, each of electrodes 17, 52, 54, and 56 can be used to gather electrophysiological data from the cardiac surface.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Figure 3:
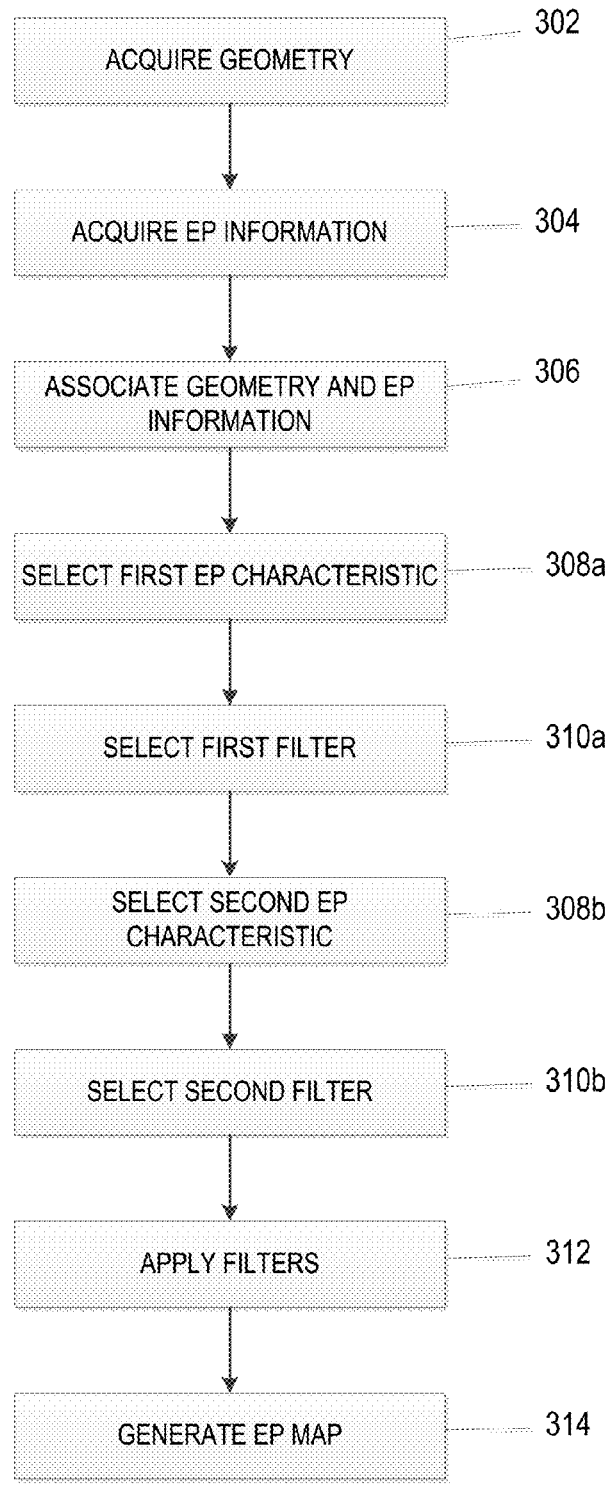
FIG. 3 is a flowchart of representative steps that can be followed to create an electrophysiology map.

FIG. 3 is a flowchart of representative steps that can be carried out to create an electrophysiology map. Advantageously, the electrophysiology maps disclosed herein can depict multiple variables (e.g., multiple cardiac electrophysiological characteristics) by location (e.g., according to their position on the surface of the heart). In some embodiments, the flowchart may represent several exemplary steps that can be carried out by the computer 20 of FIG. 1 (e.g., by one or more processors 28) to generate an electrophysiology map. It should be understood that the representative steps described below can be either hardware- or software-implemented. For the sake of explanation, the term "signal processor" is used herein to describe both hardware- and software-based implementations of the teachings herein.

In block 302, geometry information pertaining to an anatomical region (e.g., a heart chamber) is acquired. The acquired geometry information includes position information (e.g., Cartesian coordinates) for a plurality of points in the anatomical region.

The geometry can be acquired in numerous ways, many of which will be familiar to the person of ordinary skill in the art. For example, in certain aspects, system 8 is used to gather a plurality of location points that define the geometry of the anatomical region; the plurality of location points can then be used to create a model of the anatomical region. In other aspects, an external imaging modality, such as magnetic resonance imaging ("MRI"), computed tomography ("CT"), positron emission tomography ("PET"), ultrasound imaging, single-photon emission computed tomography ("SPECT"), or the like is used. It is also contemplated that multiple geometries can be acquired from multiple imaging modalities. Where multiple geometries are acquired, they can be fused or registered to a common coordinate system, for example as disclosed in U.S. application Ser. No. 11/715,923, filed 9 Mar. 2007, and/or U.S. application Ser. No. 13/087,203, filed 14 Apr. 2011, both of which are hereby incorporated by reference as though fully set forth herein.

Further, the geometry information can be time-varying. For example, cardiac geometry will vary over time with the beating of the heart. Thus, rather than acquiring a single geometry at a single point in time (e.g., max systole or max diastole), a plurality of time-varying geometries can be captured, such as by segmenting multiple phases from volumetric images captured by an MRI or CT system. These time-varying geometries can be used to create an animated geometric model of the anatomical region.

In block 304, electrophysiology information pertaining to the anatomical region is acquired. The electrophysiology information includes a plurality of electrophysiological characteristics of the anatomical region. Just as there are numerous ways to acquire the geometry information in block 302, so too are there numerous ways to acquire the electrophysiology information in block 304. For example, system 8 (e.g., electrodes 17, 52, 54, and 56 on catheter 13) can be used to measure electrical activity on the surface of the patient's heart 10. The electrophysiology information can also be time-varying.

In block 306, the geometry information acquired in block 302 is associated with the electrophysiology information acquired in block 304. For example, electrophysiology measurements made by electrodes 17, 52, 54, 56 can be associated with the position of catheter 13 at the time the measurements were made. As another example, electrophysiology measurements can be associated with locations within a CT model after the CT model has been registered to the coordinate frame of system 8. This creates a plurality of electrophysiology data points that can then be stored, for example in the memory of computer system 20, for use in the creation (and manipulation) of anatomical maps.

As mentioned above, the ordinarily skilled artisan will be familiar with numerous electrophysiology maps. For example, maps of conduction velocity and/or consistency index, such as disclosed in U.S. provisional application No. 62/063,987, filed 15 Oct. 2014, which is hereby incorporated by reference as though fully set forth herein, are both electrophysiology maps. Other electrophysiology maps include, without limitation, complex fractionated electrogram ("CFE") maps (e.g., maps of cycle length mean and cycle length standard deviation), fractionation index maps, peak-to-peak voltage maps, lateness maps (e.g., Late-P and Late-A), local activation time ("LAT") maps, and electrogram ("EGM") sharpness maps.

It is known to show a single electrophysiological characteristic per electrophysiology map. However, with the proliferation of electrophysiological characteristics that may be of interest to a practitioner during an electrophysiology study, a one-characteristic-per-map approach can become cumbersome.

Likewise, it is known to display a full range of values for an electrophysiological characteristic on an electrophysiology map (e.g., displaying peak-to-peak voltages from the lowest value measured within the anatomical region to the highest value measured within the anatomical region). This requires the presentation scale (e.g., color scale, monochrome scale, or other graphical convention) to be spread over a relatively large range. A practitioner may, however, be interested only in a narrower range of values for the electrophysiological characteristic. For example, U.S. patent application Ser. No. 14/504,174, filed 1 Oct. 2014 and hereby incorporated by reference as though fully set forth herein, describes the use of upper and lower bounds on the use of a presentation scale for lateness attributes.

According to an aspect of the instant disclosure, multiple electrophysiology characteristics can be presented on a single electrophysiology map. According to another aspect of the instant disclosure, the user can set various filters (e.g., high-pass, low-pass, band-pass, band-reject) on the presentation of the electrophysiological characteristics, such that only certain ranges of values for given electrophysiological characteristics are displayed.

Thus, in steps 308a, 308b, respectively, a user can select a first electrophysiology characteristic (e.g., cycle length mean) and a second electrophysiology characteristic (e.g., cycle length standard deviation) to display in an electrophysiology map.

Similarly, in steps 310a, 310b, respectively, the user can set first and second filter criteria corresponding, respectively, to the selected first and second electrophysiology characteristics. For example, the user can choose to apply a band-pass filter of 150 ms to 250 ms to the CFE cycle length mean and a band-pass filter of 1 ms to 30 ms to the CFE cycle length standard deviation.

The selected filters are applied to the plurality of EP data points in block 312. In certain aspects, the output of the filters is a subset of the plurality of EP data points that meet both the filtering criteria set in blocks 310a, 310b. That is, the filters can be applied to the plurality of EP data points with a Boolean AND. In other aspects, the output of the filters is a subset of the plurality of EP data points that meet either of the filtering criteria set in blocks 310a, 310b. That is, the filters can be applied to the plurality of EP data points with a Boolean OR. It is also contemplated that the application of the filters can yield two subsets: a first subset that satisfies the first filtering criterion of block 310a and a second subset that satisfies the second filtering criterion of block 310b.

An electrophysiology map is rendered in block 314. The electrophysiology map is a graphical representation of the subset of the plurality of EP data points that results from the application of the first and second filters in block 312. Thus, for example, the acquired geometry (or geometries) can be rendered graphically (e.g., using techniques that are familiar to those of ordinary skill in the art), and a map of the electrophysiology characteristics, post-filtering, can be superimposed thereon.

Figure 4A:
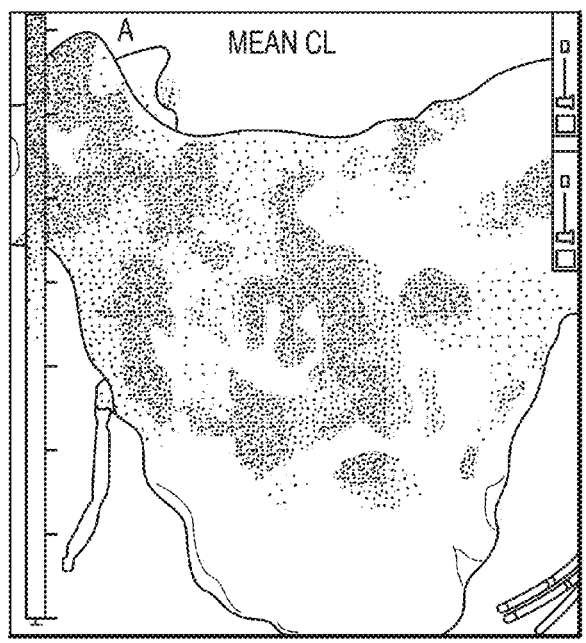
FIGS. 4a through 4d illustrate the application of the EP data point filtering teachings herein to maps of cycle length mean and cycle length standard deviation.
Figure 4B:
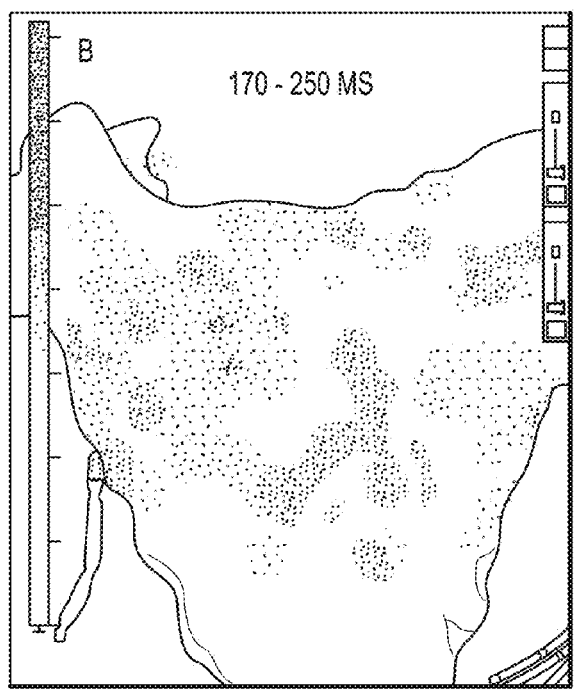
Figure 4C:
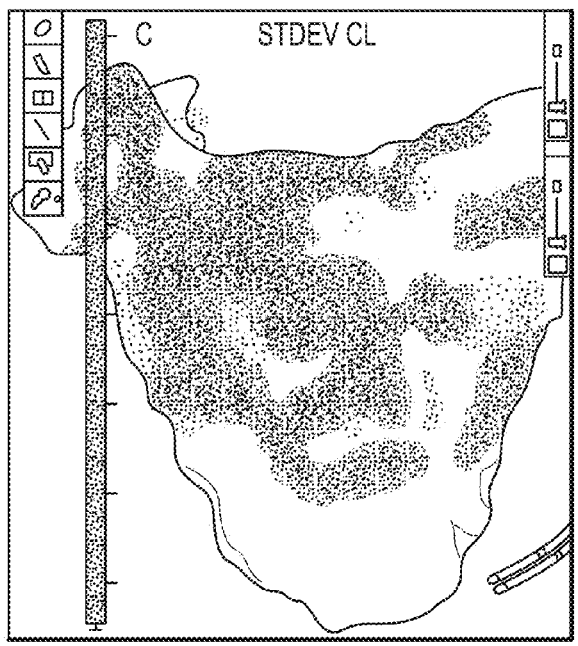

FIGS. 4a through 4d and 5a through 5c illustrate the foregoing teachings. FIG. 4a is a traditional cycle length mean map without a filter applied, while FIG. 4b applies a band-pass filter having a pass band of 170 ms to 250 ms to the map of FIG. 4a. Similarly, FIG. 4c is a traditional cycle length standard deviation map without a filter applied, while FIG. 4d applies a band-pass filter having a pass band of 1 ms to 40 ms to the map of FIG. 4c.

Figure 4D:
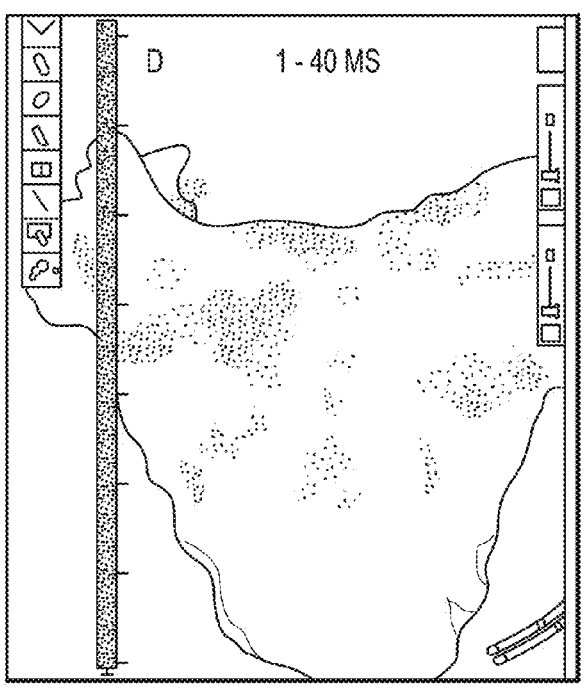

As can be seen by comparing FIGS. 4a and 4c, on the one hand, to FIGS. 4b and 4d, on the other hand, only the regions having values of interest are mapped in FIGS. 4b and 4d. The same range of colorscale values is thus applied over a narrower numerical range in FIGS. 4b and 4d than in FIGS. 4a and 4c, allowing a more refined presentation in FIGS. 4b and 4d relative to FIGS. 4a and 4c (that is, more subtle variations in the depicted electrophysiological characteristic can be depicted in FIGS. 4b and 4d than in FIGS. 4a and 4c).

Figure 5A:
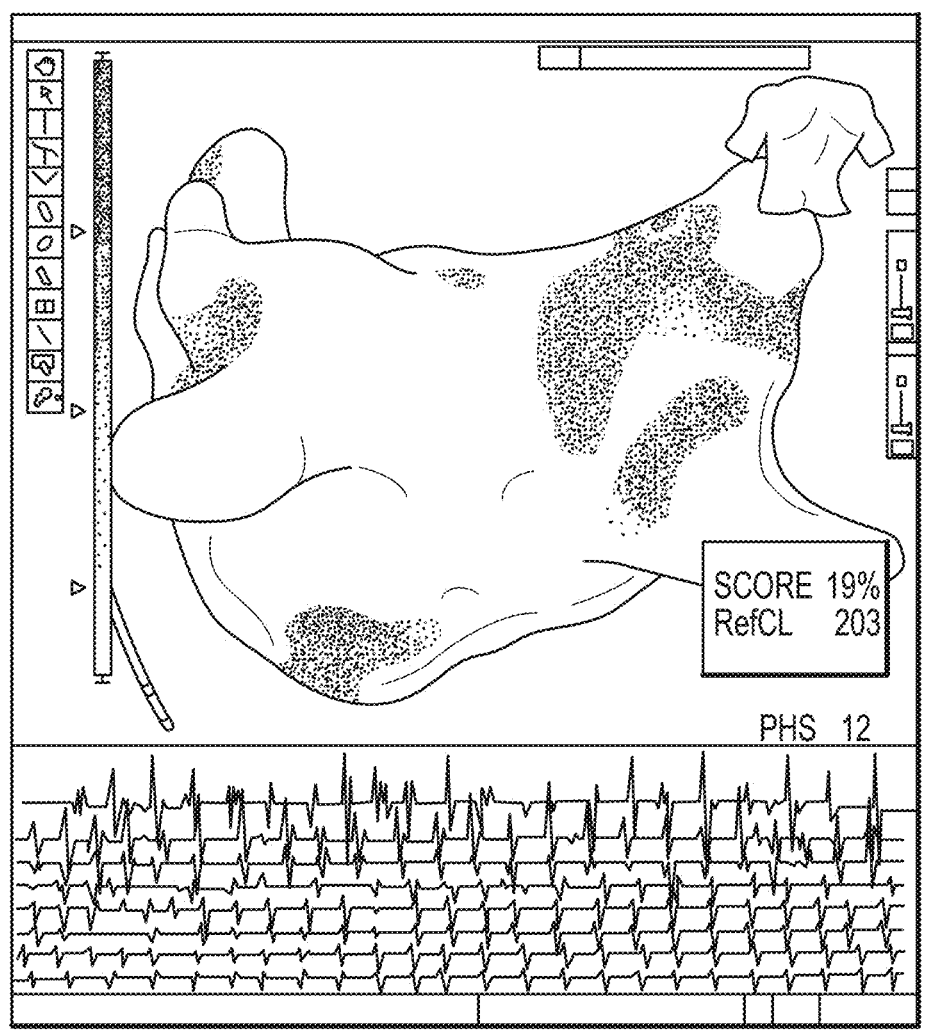
Figure 5C:
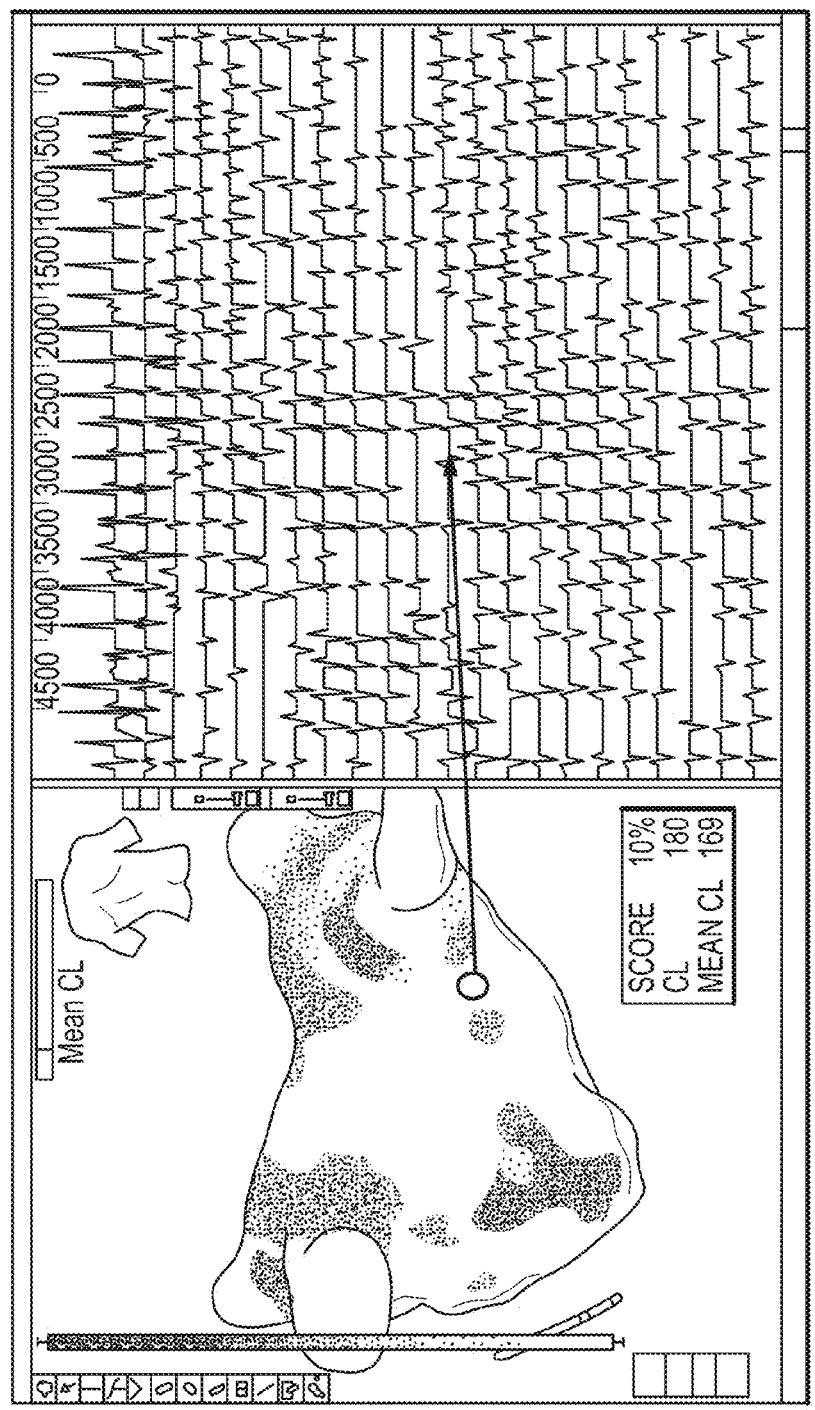

Turning now to FIGS. 5a through 5c, suppose that a practitioner is interested in identifying regions of cardiac tissue that exhibit fast and regular activation. Such regions could, for example, be defined as regions that exhibit both a cycle length mean between 150 ms and 250 ms and a cycle length standard deviation between 1 ms and 30 ms. FIG. 5a, therefore, is an exemplary electrophysiology map that graphically presents only those EP data points meeting both criteria (i.e., EP data points having a cycle length mean between 150 ms and 250 ms and a cycle length standard deviation between 1 ms and 30 ms). The advantages of such a presentation are similar to those discussed above with respect to FIGS. 4a-4d. In particular, FIG. 5b illustrates the types of EP data points that are included in the map of FIG. 5a (that is, EP data points that exhibit electrophysiological characteristics of interest to the practitioner), while FIG. 5c illustrates the types of EP data points that are excluded in the map of FIG. 5c (that is, EP data points that do not exhibit electrophysiological characteristics of interest to the practitioner).

Figure 6B:
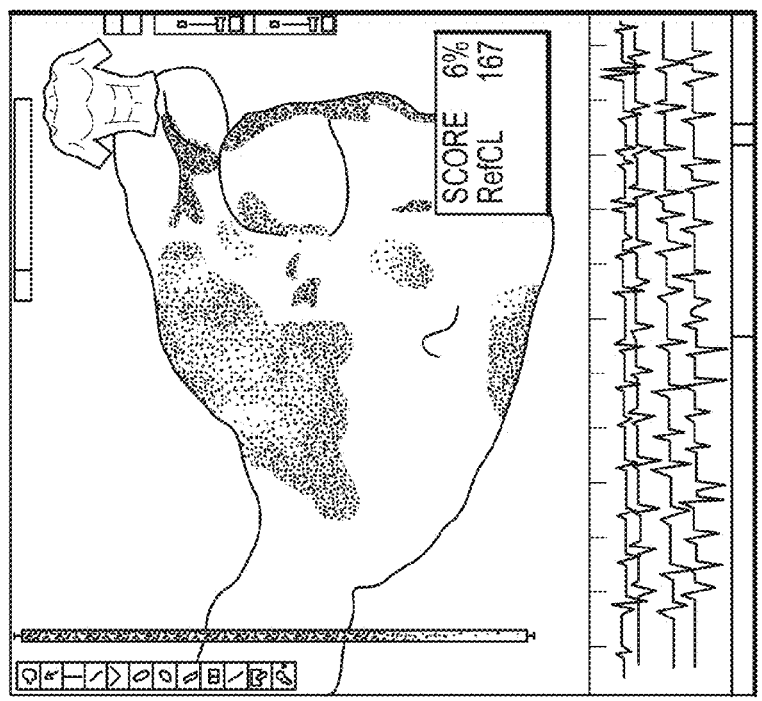
FIGS. 6a and 6b illustrate the application of the EP data point filtering teachings herein to a map of fractionation index.
Figure 6A:
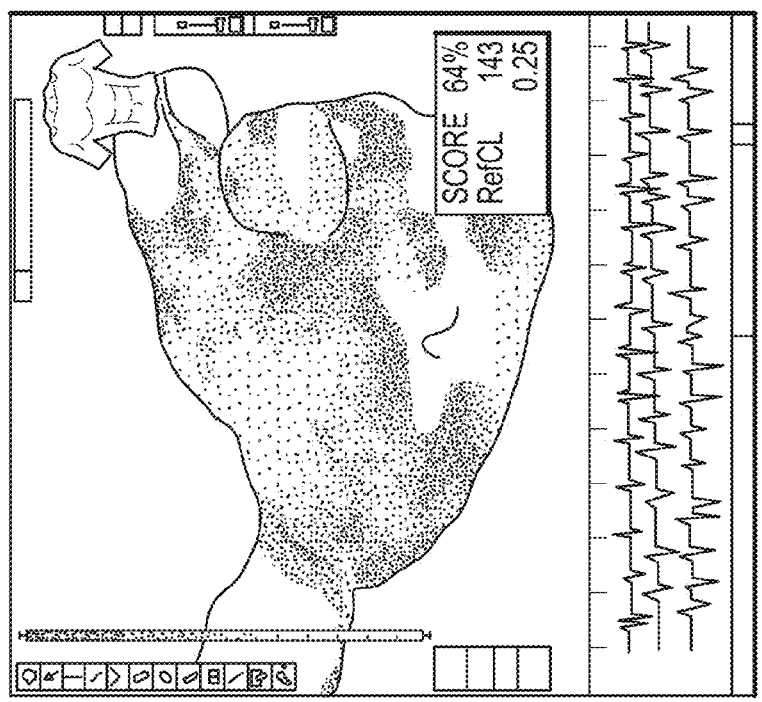
Figure 7B:
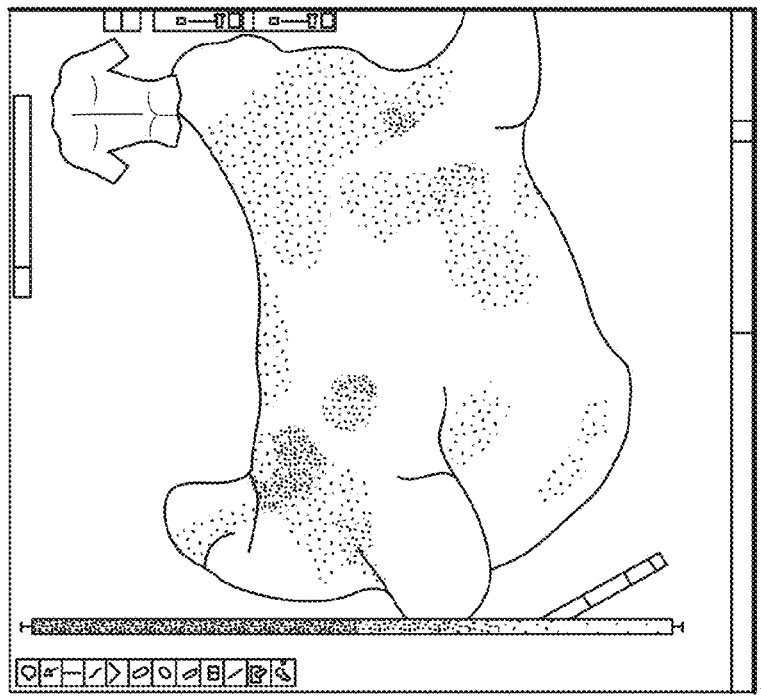
FIGS. 7a and 7b illustrate the application of the EP data point filtering teachings herein to a map of conduction velocity.
Figure 7A:
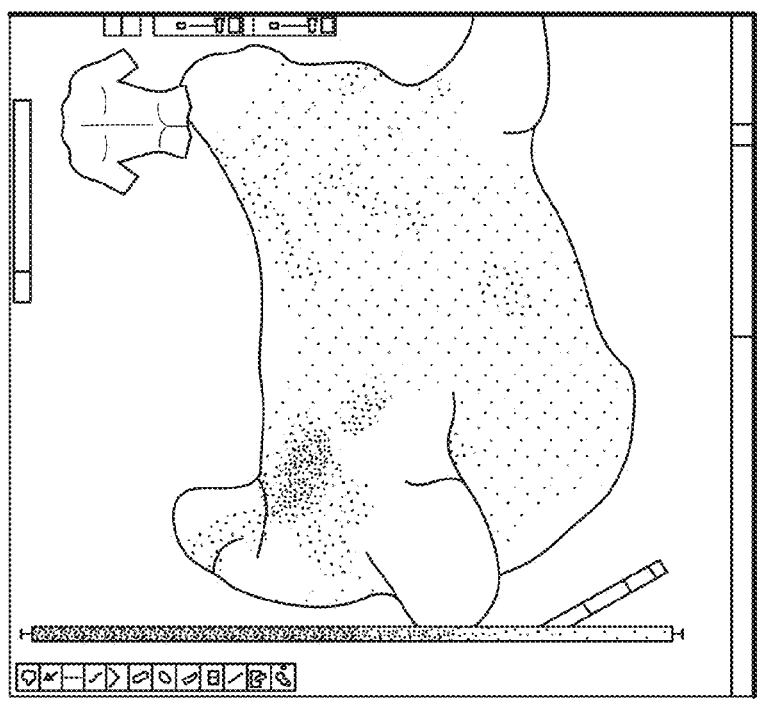

It should be understood that FIGS. 4a-4d and 5a-5c are merely exemplary of the present teachings. In other embodiments, a user might select the following electrophysiology characteristics and associated filters:

Using a high pass filter and a map of fractionation index to identify areas with high fractionation, which may be critical substrates for the perpetuation of atrial fibrillation, and thus desirable targets for ablation to treat the same (compare FIG. 6a with FIG. 6b);

Using a low pass filter and a map of peak-to-peak voltage to identify areas with low peak-to-peak voltage; areas of low voltage can indicate fibrosis or scarring, which can serve as a substrate for arrhythmia maintenance;

Using a high pass filter and a map of electrogram sharpness to identify areas with high sharpness, which might be indicative of an ectopic focus;

Using a high pass filter and a map of conduction velocity consistency index to identify regions where the direction of the propagating activation wavefront is highly consistent, which can highlight a wavefront circuit in an atrial arrhythmia; and/or Using a low pass filter and a map of conduction velocity to identify regions of slow conduction; because slow conduction is a hallmark of maintaining a reentrant circuit, the regions identified by such a map can be targeted for ablation therapy in the treatment of ventricular tachycardia ("VT") (compare FIG. 7a with FIG. 7b).

Of course, even this list of embodiments is non-exhaustive, and the person of ordinary skill in the art would readily appreciate how to extend the teachings herein to additional electrophysiology maps and combinations of electrophysiology maps.

Figure 8A:
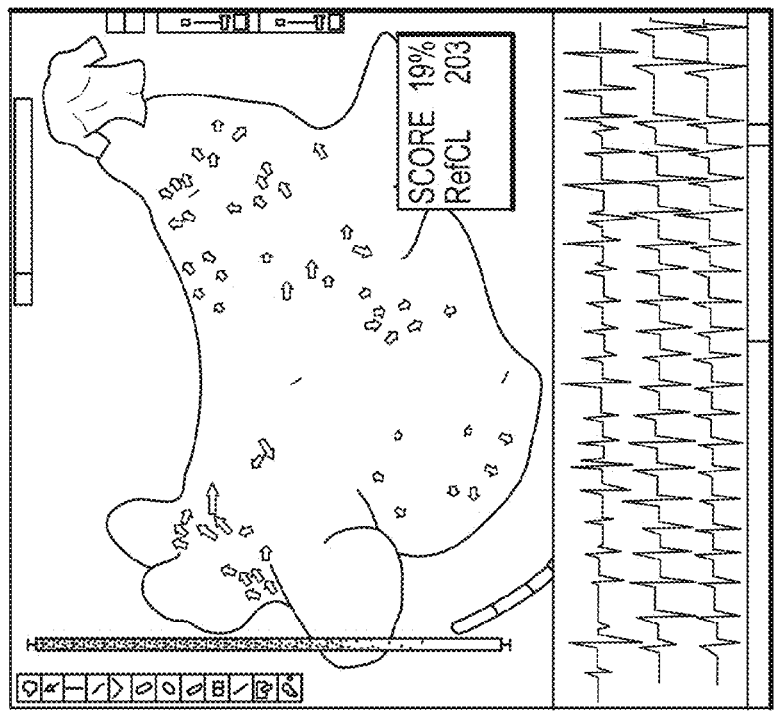
FIGS. 8a and 8b illustrate the application of the EP data point filtering and electrophysiology map combination teachings herein to a map of the magnitude, direction, and consistency of local conduction velocity.
Figure 8B:
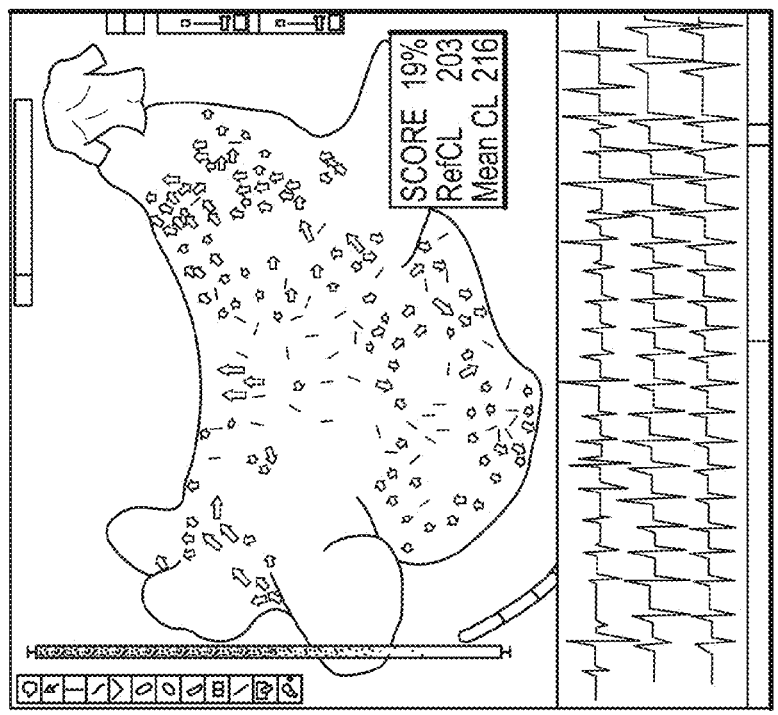

Similarly, various conventions can be used to present the various combinations of electrophysiology maps discussed herein. For example, various combinations of full color and monochrome scales (e.g., grey scale, brown scale) can be used in the display of electrophysiology maps. Various iconography can also be used. For example, FIGS. 8a (unfiltered) and 8b (high pass filtered for consistency index) illustrate the use of arrowheads to depict activation direction (direction of arrow), local conduction velocity (length of arrow), and consistency index (width of arrow). In an alternative embodiment, a zig-zag line can be used instead of an arrowhead to represent conduction velocity, with a tighter zig-zag reflecting a lower conduction velocity. Still other methods of presenting electrophysiology maps are disclosed in U.S. provisional application No. 61/936,954, filed 7 Feb. 2014, which is hereby incorporated by reference as though fully set forth herein.

Where multiple different electrophysiology characteristics are to be displayed on a single electrophysiology map, the user can assign priorities to the various characteristics. Once the characteristics are prioritized, any regions of overlap can be rendered according to the relative priorities of the characteristics, with higher priority characteristics drawn preferentially to lower priority characteristics. Stated another way, if a particular EP data point includes data for multiple electrophysiology characteristics that satisfy the user-specified filters, the EP data point will be displayed with the highest priority electrophysiology characteristic.

Figure 9B:
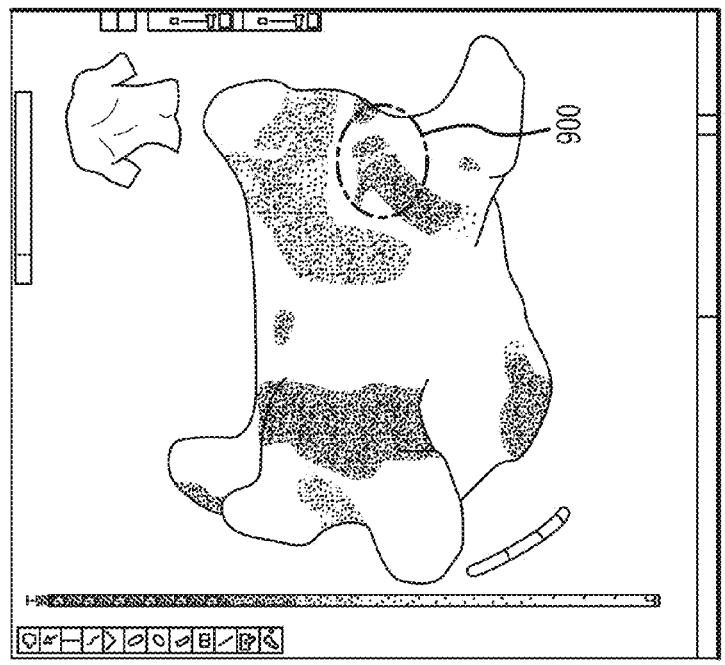
FIGS. 9a and 9b illustrate the application of the display prioritization teachings herein to a map of cycle length mean, cycle length standard deviation, and peak-to-peak voltage.
Figure 9A:
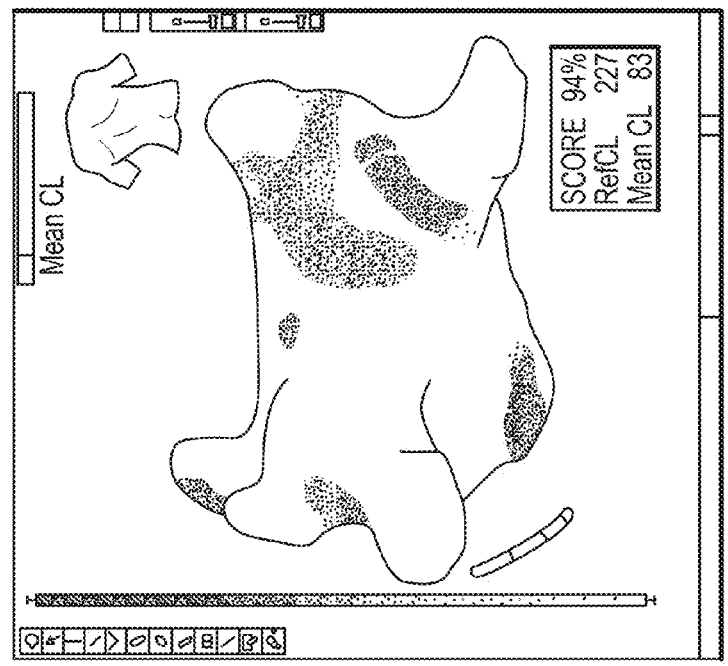

For example, FIG. 9a is similar to FIG. 5a in that it depicts a map of EP data points that have been band pass filtered for cycle length mean and standard deviation. In FIG. 9b, a low pass filtered peak-to-peak map is added to the map of FIG. 9a, with the peak-to-peak map having a higher priority. Thus, where the two maps overlap (that is, where EP data points satisfy both the cycle length and peak-to-peak filters), the peak-to-peak map is drawn instead of the cycle length map (see region 900).

Figure 10:
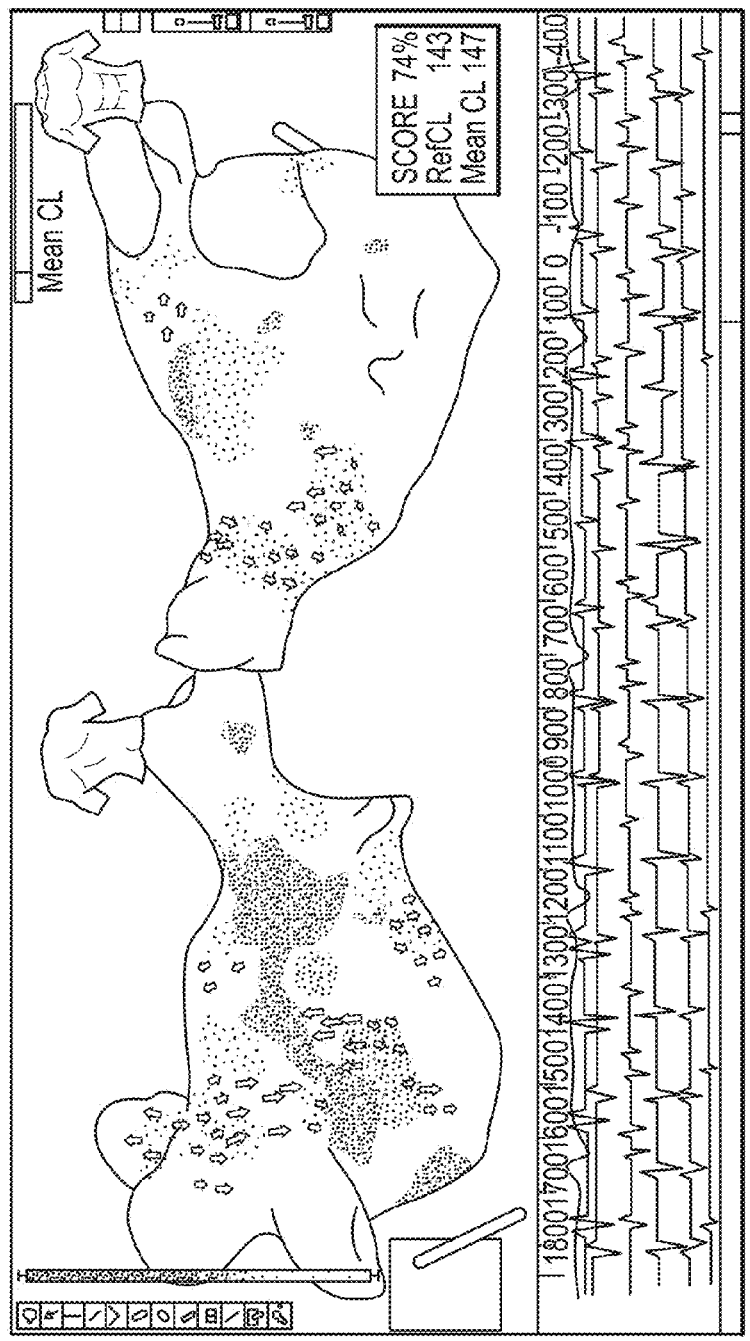
FIG. 10 is another electrophysiology map that illustrates the display prioritization teachings herein.

FIG. 10 is another exemplary prioritized electrophysiology map. The map of FIG. 10 includes as the highest priority a low pass filtered peak-to-peak map, as the next highest priority a high pass filtered fractionation index map, and as the lowest priority a band pass filtered map of cycle length mean and standard deviation as described above. FIG. 10 also includes conduction velocity arrows that have been high pass filtered for consistency index and star icons indicative of focal activity as identified using high pass filtered sharpness data.

Although several embodiments of this invention have been described above with a certain degree of particularity, those skilled in the art could make numerous alterations to the disclosed embodiments without departing from the spirit or scope of this invention.

For example, although the electrophysiology maps disclosed herein have been described in the context of a two-characteristic (and, similarly, two-filter) map, the ordinarily skilled artisan will appreciate how to extend the teachings herein to any n-characteristic and/or n-filter map, where n is an integer greater than 1.

As another example, although some of the filtering methods described above are applied with Boolean ANDs and Boolean ORs, the teachings herein could be adapted to other relationships between characteristics (e.g., filtered characteristic one AND NOT (filtered characteristic two OR filtered characteristic three)).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating an electrophysiology map, comprising:
    acquiring geometry information pertaining to an anatomical region, the geometry information comprising position information for a plurality of points in the anatomical region;
    acquiring electrophysiology information pertaining to the anatomical region, the electrophysiology information comprising a plurality of electrophysiological characteristics of the anatomical region;
    associating the geometry information with the electrophysiology information as a plurality of electrophysiology ("EP") data points;
    accepting user input to select a first electrophysiological characteristic of the plurality of electrophysiological characteristics and a first filtering criterion for the first electrophysiological characteristic;
    accepting user input to select a second electrophysiological characteristic of the plurality of electrophysiological characteristics and a second filtering criterion for the second electrophysiological characteristic;
    applying the first filtering criterion and the second filtering criterion to the plurality of EP data points;
    outputting a subset of the plurality of EP data points satisfying both the first filtering criterion and the second filtering criterion;
    accepting user input prioritizing the first electrophysiological characteristic and the second electrophysiological characteristic; and
    outputting a three-dimensional graphical representation of the subset of the plurality of EP data points,
    wherein the three-dimensional graphical representation includes both the first electrophysiological characteristic and the second electrophysiological characteristic, and
    wherein a higher priority electrophysiological characteristic of the first and second electrophysiological characteristics is rendered preferentially to and to the exclusion of a lower priority electrophysiological characteristic of the first and second electrophysiological characteristics in regions of overlap between the first electrophysiological characteristic and the second electrophysiological characteristic.

2. The method according to claim 1, wherein the first electrophysiological characteristic comprises cycle length mean and the second electrophysiological characteristic comprises cycle length standard deviation.

3. The method according to claim 2, wherein the first filtering criterion comprises a band pass filter with a pass band from 110 ms to 290 ms and second filtering criterion comprises a band pass filter with a pass band from 1 ms to 30 ms.

4. The method according to claim 1, wherein the first electrophysiological characteristic and the first filtering criterion respectively comprise one of: fractionation index and a high pass filter; peak-to-peak voltage and a low pass filter; electrogram sharpness and a high pass filter; conduction velocity consistency index and a high pass filter; and conduction velocity and a low pass filter.

5. The method according to claim 4, wherein the second electrophysiological characteristic and the second filtering criterion respectively comprise one of: fractionation index and a high pass filter; peak-to-peak voltage and a low pass filter; electrogram sharpness and a high pass filter; conduction velocity consistency index and a high pass filter; and conduction velocity and a low pass filter, and wherein the second electrophysiological characteristic and the second filtering criterion differ, respectively, from the first electrophysiological characteristic and the first filtering criterion.

6. A method of generating an electrophysiology map, comprising:
acquiring geometry information pertaining to an anatomical region, the geometry information comprising position information for a plurality of points in the anatomical region;
acquiring electrophysiology information pertaining to the anatomical region, the electrophysiology information comprising a plurality of electrophysiological characteristics of the anatomical region;
associating the geometry information with the electrophysiology information as a plurality of electrophysiology ("EP") data points;
accepting user input to select a first electrophysiological characteristic of the plurality of electrophysiological characteristics, a first filtering criterion for the first electrophysiological characteristic, and a first priority for the first electrophysiological characteristic;
applying the first filtering criterion to the plurality of EP data points to output a first subset of the plurality of EP data points satisfying the first filtering criterion;
accepting user input to select a second electrophysiological characteristic of the plurality of electrophysiological characteristics, a second filtering criterion for the second electrophysiological characteristic, and a second priority for the second electrophysiological characteristic;
applying the second filtering criterion to the plurality of EP data points to output a second subset of the plurality of EP data points satisfying the second filtering criterion;
outputting a three-dimensional graphical representation of the first and second subsets of the plurality of EP data points according to the first priority and the second priority such that, in regions of overlap between the first and second subsets of the plurality of EP data points, a higher priority subset of the first and second subsets of the plurality of EP data points is rendered preferentially to and to the exclusion of a lower priority subset of the plurality of EP data points.

7. The method according to claim 6, wherein outputting a three-dimensional graphical representation of the first and second subsets of the plurality of EP data points according to the first priority and the second priority comprises:
rendering the graphical representation of the first subset of the plurality of EP data points preferentially to the graphical representation of the second subset of the plurality of data points if the first priority is higher than the second priority; and
rendering the graphical representation of the second subset of the plurality of EP data points preferentially to the graphical representation of the first subset of the plurality of data points if the second priority is higher than the first priority.

8. The method according to claim 6, wherein outputting a three-dimensional graphical representation of the first and second subsets of the plurality of EP data points according to the first priority and the second priority comprises:
rendering the graphical representation of the first subset of the plurality of data points using a colorscale; and
rendering the graphical representation of the second subset of the plurality of data points using a monochrome scale.

9. The method according to claim 6, wherein outputting a three-dimensional graphical representation of the first and second subsets of the plurality of EP data points according to the first priority and the second priority comprises:
rendering the graphical representation of the first subset of the plurality of data points using one of a colorscale and a monochrome scale; and
rendering the graphical representation of the second subset of the plurality of data points using iconography.

10. The method according to claim 6, further comprising:
accepting user input to select a third electrophysiological characteristic of the plurality of electrophysiological characteristics, a third filtering criterion for the third electrophysiological characteristic, and a third priority for the third electrophysiological characteristic;
applying the third filtering criterion to the plurality of EP data points to output a third subset of the plurality of EP data points satisfying the third filtering criterion; and
outputting a three-dimensional graphical representation of the third subset of the plurality of EP data points according to the third priority.

11. The method according to claim 10, wherein one of the graphical representations of the first, second, and third subsets of the plurality of EP data points is output in colorscale and two of the graphical representations of the first, second, and third subsets is output in monochrome scale.

12. A system for generating an electrophysiology map, comprising:
an electrophysiology data point processor configured to accept as input geometry information and electrophysiology information pertaining to an anatomical region and to associate the geometry information with the electrophysiology information as a plurality of electrophysiology data points;
a filtering processor configured to accept as input a user's selection of n electrophysiological characteristics, wherein each of the n selected electrophysiological characteristics has an associated filtering criterion and an associated priority, and to apply the filtering criteria to their respective ones of the n selected electrophysiological characteristics; and a mapping processor configured to output a three-dimensional representation of the filtered n selected electrophysiological characteristics according to their respective priorities, wherein the three-dimensional representation includes each of the filtered n selected electrophysiological characteristics, and wherein a highest priority electrophysiological characteristic of the filtered n selected electrophysiological characteristics is rendered preferentially to and to the exclusion of lower priority electrophysiological characteristics of the filtered n selected electrophysiological characteristics in regions of overlap.

* * * * *